(12) United States Patent
Jährling

(10) Patent No.: US 7,650,656 B2
(45) Date of Patent: Jan. 26, 2010

(54) SUPPORT MAT FOR A TRAUMA PATIENT

(75) Inventor: Peter Jährling, Puschendorf (DE)

(73) Assignee: Siemens Aktiengesellschaft, Munich (DE)

( * ) Notice: Subject to any disclaimer, the term of this patent is extended or adjusted under 35 U.S.C. 154(b) by 597 days.

(21) Appl. No.: 11/031,799

(22) Filed: Jan. 7, 2005

(65) Prior Publication Data

US 2005/0198736 A1    Sep. 15, 2005

(30) Foreign Application Priority Data

Jan. 9, 2004    (DE)    ........................ 10 2004 001 614

(51) Int. Cl.
*A61G 1/01*    (2006.01)
(52) U.S. Cl. ..................... 5/601; 5/482; 5/497
(58) Field of Classification Search ............. 5/601, 5/482, 494, 497, 498
See application file for complete search history.

(56) References Cited

U.S. PATENT DOCUMENTS

| | | | | |
|---|---|---|---|---|
| 1,913,750 A | * | 6/1933 | Frank | 5/499 |
| 4,993,092 A | * | 2/1991 | Weeks | 5/658 |
| 5,400,448 A | * | 3/1995 | Zwickey | 5/691 |
| 5,509,718 A | * | 4/1996 | Neary | 297/228.12 |
| 6,128,796 A | * | 10/2000 | McCormick et al. | 5/626 |

FOREIGN PATENT DOCUMENTS

DE    80 16 753 U1    11/1980

\* cited by examiner

*Primary Examiner*—Fredrick Conley

(57) ABSTRACT

The invention relates to a support mat (1) for a trauma patient (16) with a seamlessly welded cover (22), the sides of which are provided with skirt-like overhangs (2 to 5). In this manner the support mat (1) and modality protection are combined in a single component. In the folded over state, the mat protects the patient visually on the one hand and against heat loss on the other hand. Furthermore the extremities are thus secured during transportation and also during CT examinations. In the folded open state, the mat protects the modalities from fluids.

19 Claims, 4 Drawing Sheets

SUPPORT MAT FOR A TRAUMA PATIENT

CROSS REFERENCE TO RELATED APPLICATIONS

This application claims priority to the German application No. 10 2004 001 614.3, filed Jan. 9, 2004 which is incorporated by reference herein in its entirety.

FIELD OF INVENTION

The invention relates to a support mat for a trauma patient.

BACKGROUND OF INVENTION

Support mats of this type are required for supporting trauma patients on different modalities and tables or transporters, for the purpose of diagnosis or therapy. To this end, the patient is to be supported in such a manner that bedsores, heat loss and support pain are avoided. Furthermore a support aid of this sort should comprise high X-ray transparency and ensure the possibility of simple disinfection.

SUMMARY OF INVENTION

The extensive fluid losses, which occur with trauma patients of this type, represent a further problem for the modalities and the clinical environment. Fluids such as blood from patients or infusions can penetrate the modalities, which, for reasons of functionality, may not be completely sealed. The cleaning of these types of contaminated modalities with fluid disinfectant agents is a further drawback.

According to existing clinical information, the majority of patients are only supported on thin support mats without covering the modalities. The patient is warmed, if at all, by means of red light emitters or the like, whereby no warming can take place during transportation. X-ray transparency is achieved by means of thin mat thicknesses, which provide no protection against bedsores.

DE 80 16 753 U1 discloses an emergency and protective sheet for the injured and sick, having a heat insulating and/or absorbent base, and enveloping lateral sections connected on both sides to a central sheet section, separated respectively from the lateral head sections by means of an approximately wedge-shaped lateral cut-out. Such a cover is only used for transportation and intermediate support for an injured patient.

An object of the invention is to produce a support mat of the type mentioned above, said mat being designed such that the aforementioned support problem is solved together with the protection problem.

The object is achieved by the claims. Such a support mat combines a support mat and modality protection in a single component. Folded over, the mat protects the patient visually on the one hand and against heat loss on the other hand. Furthermore the extremities are secured during transportation and also during a CT examination. Folded open, the mat protects the modalities from fluid.

It has proven to be advantageous for the cover and/or overhangs to be made from polyurethane.

According to the invention, the overhangs can be of differing lengths.

During transportation the environment is also kept free of fluids if the overhangs are designed such that the whole body length of the patient lying on the support mat can be covered in an overlapping manner, whereby the overhangs can be connected to one another laterally by means of gussets. With the overhands folded over a type of sleeping bag is formed so that no fluid can escape.

The overhangs can be advantageously provided with gussets at the edges.

The trauma patient is effectively supported, if the support mat is made from foam.

Unobstructed access to the head of the patient is achieved for the anesthesiology process, if the head section is designed as a type of open hood, or an open hood is attached to the head section.

According to the invention, the foot section can be of a short design.

Fluids cannot penetrate the modalities if the overhangs are designed such that during diagnosis or therapy on different modalities, the overhangs can be folded away from the patient such that the modalities can be covered.

BRIEF DESCRIPTION OF THE DRAWINGS

The invention is described in further detail below, with reference to the exemplary embodiments shown in the drawing, in which.

DETAILED DESCRIPTION OF INVENTION

Figure 1:
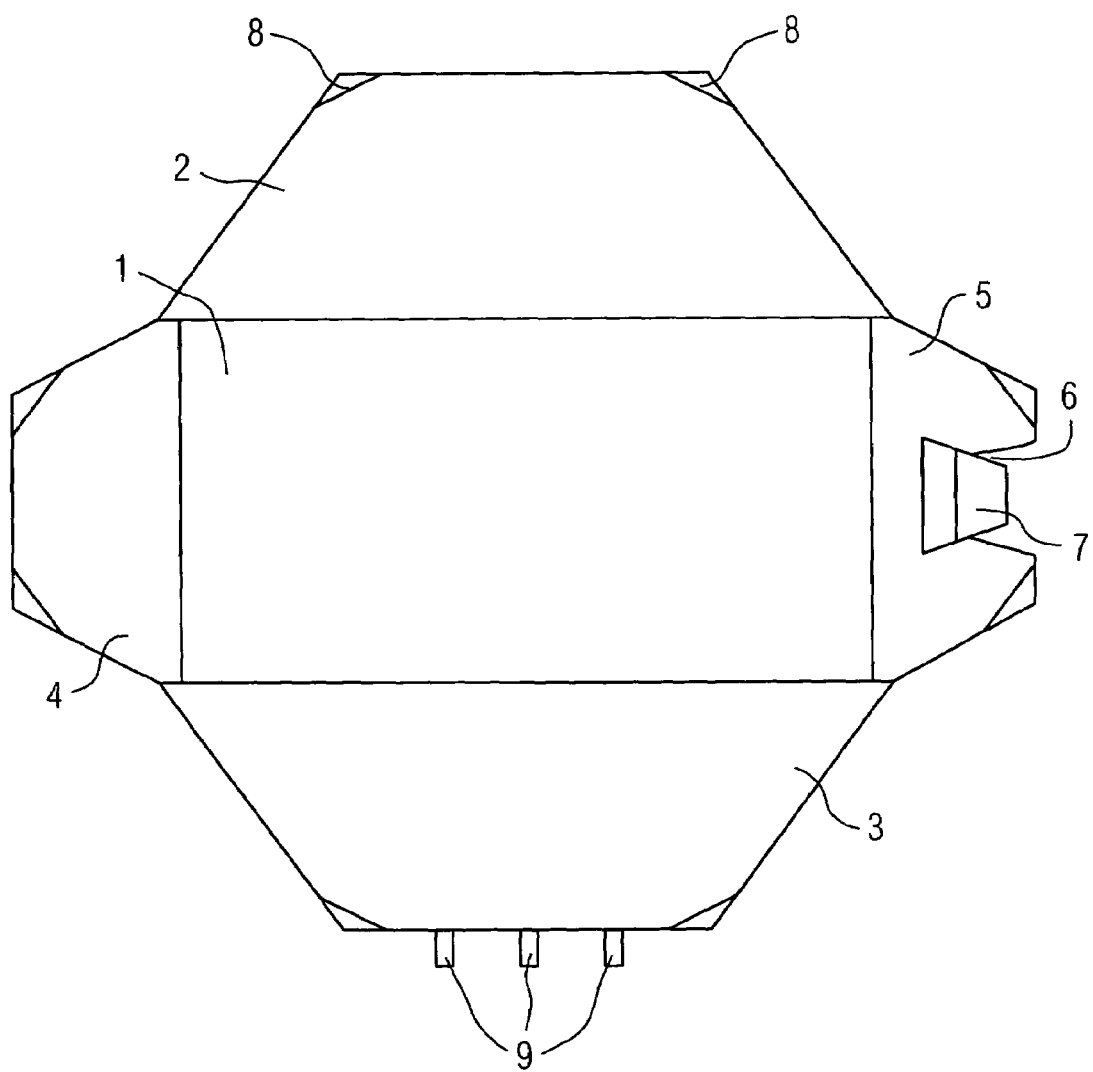
FIG. 1 shows the top view of a support mat according to the invention.

A support mat 1 for a patient made from relatively hard foam is shown in FIG. 1, which is provided with a seamlessly welded cover. Skirt-like overhangs 2 to 5 are attached to the underside of the support mat 1. The lateral overhangs 2 and 3 are designed as trapezoidal for instance and are of such a length that they overlap over a patient when folded together. The foot section 4 is similarly trapezoidal but is shorter. The basic shape of the head section 5 is also trapezoidal but it has cut-outs 6 on its outer edge, in which a hood 7 is attached. For reinforcement purposes the corners of the overhangs 2 to 5 are provided with gussets 8. One of the lateral overhangs 2 and 3 is provided with a tab as a fastener 9, which can be configured in a known manner as a hook and loop type fastener, whereby the tab acts on a fastener element (not shown) arranged on the other lateral overhang 2 or 3.

A relatively hard foam is a foam, whereby the support mat 1 is not fully compressed under the body weight of a trauma patient, so that the patient does not rest on the support plate of a modality for example. This foam does not need to have a bearing function, thus it does not replace a support plate such as a table or transporter for example.

Figure 2:
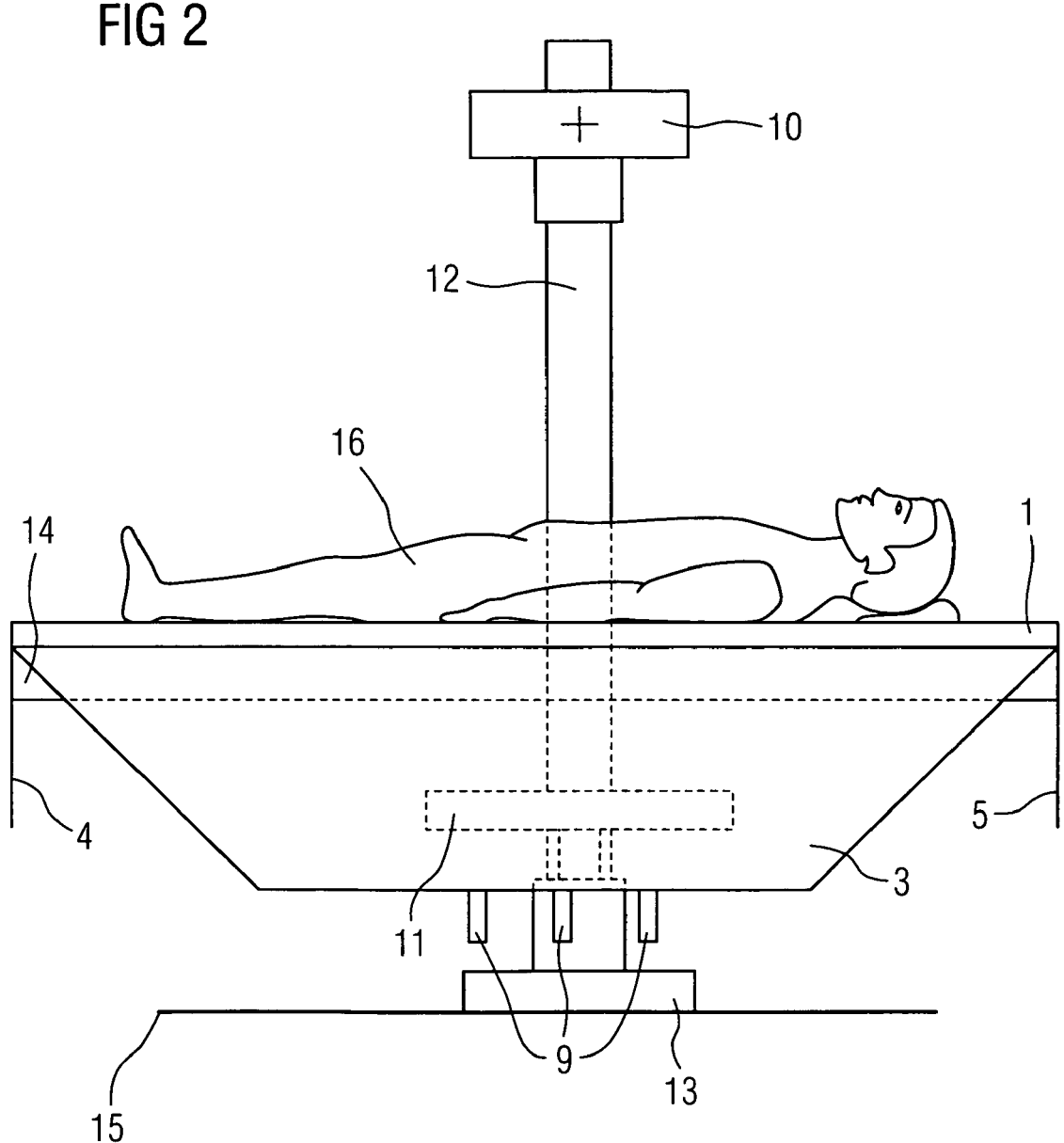
FIG. 2 shows the support mat spread out according to FIG. 1, on a patient carrying table of a modality.

FIG. 2 shows a modality with an X-ray emitter 10 and an X-ray detector 11, which are linked to one another by means of a C-arm 12. The modality is fixed to the ground 15 by means of a column 13. It further comprises a patient support table 14, on which the support mat 1 is arranged. A patient 16 to be examined is located thereon. The sections 11 to 14 of the modality are protected against fluids by means of the open overhangs 2 to 5.

Figure 3:
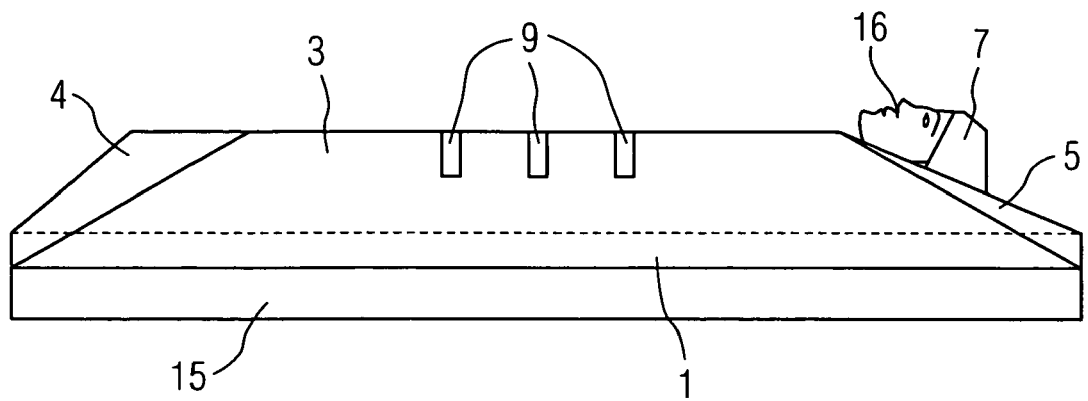
FIG. 3 shows the support mat according to FIG. 2 folded together.

FIG. 3 shows the support mat 1, the overhangs 2 to 5 of which cover the patient, thereby warming said patient. At the same time, the formation of a sleeping bag type cover prevents fluid such as blood from the trauma patient 16 or infusions escaping. The open hood 7 leaves the patient's 16 face free, so that an anesthetist has free access to said trauma patient 16.

Figure 4:
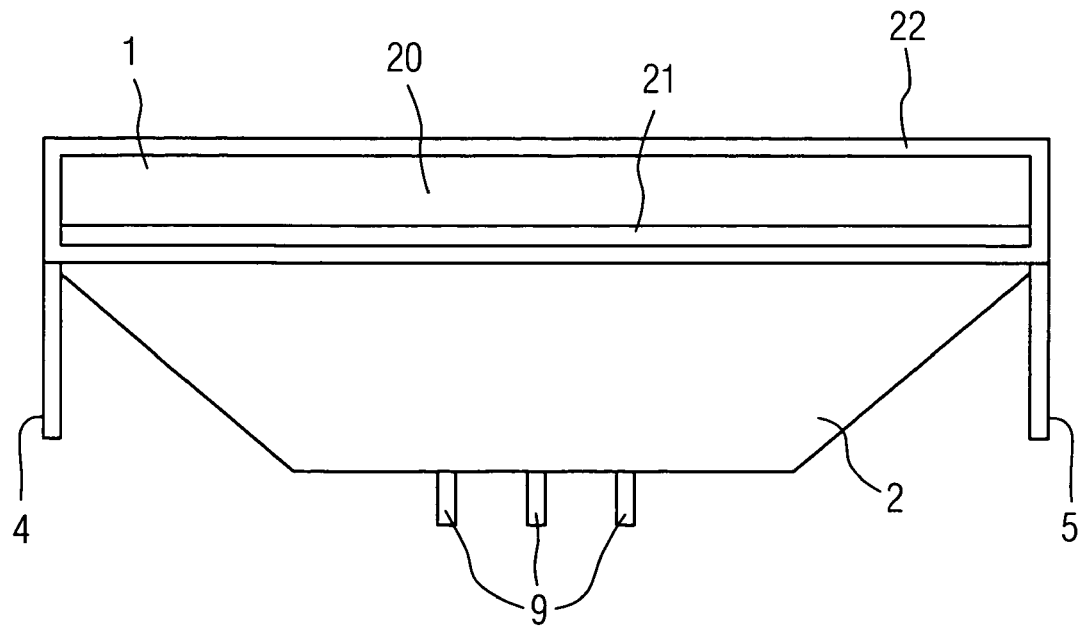
FIG. 4 shows a cross-section through a support mat according to FIG. 2.

FIG. 4 shows a cross-sectional view of the support mat 1 for the trauma patient 16 with a core 20 made from relatively hard foam, which can rest on a board 21 for stability purposes, made for instance from carbon fiber. The support mat 1 is provided with a seamlessly welded cover 22, which is made from polyurethane for example. The schematically represented skirt-like overhangs 2 to 5 are attached to the lower side of the support mat 1 and can also be made from polyurethane. The board 21 can be dispensed with in the case of a sufficiently hard foam but it must be ensured that the foam does not become too hard for the trauma patient 16.

Figure 5:
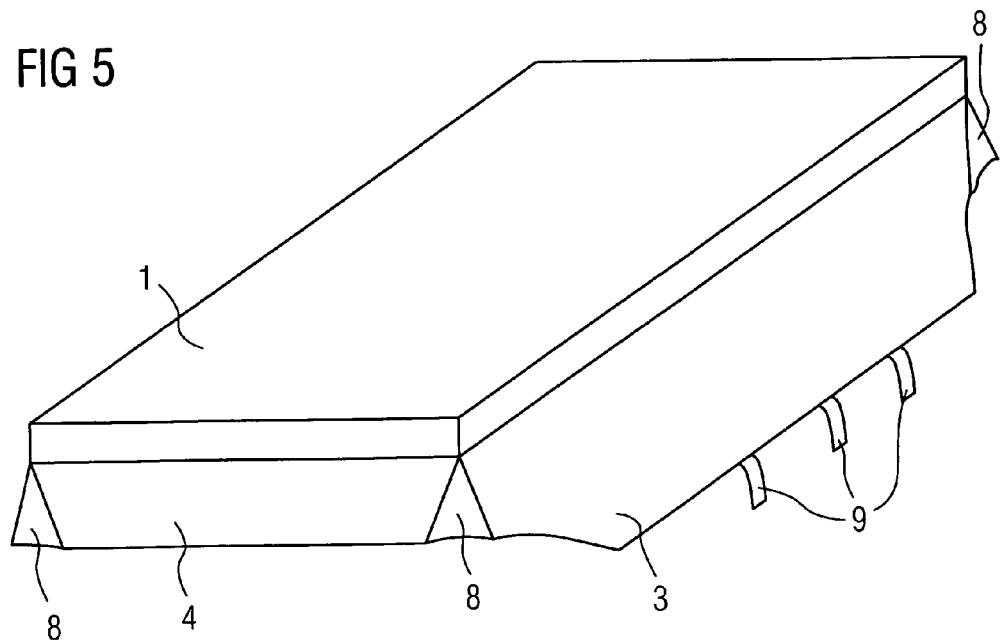
FIG. 5 shows a further embodiment of an inventive support mat in the open state and FIG. 6 shows the support mat according to FIG. 5 folded together.

FIG. 5 shows a further embodiment of a support mat 1 according to the invention in the folded open state. It is essential here that the gussets 8 form a connection between the individual overhangs 2 to 5, so that a type of sleeping bag is formed in the folded over state, thus ensuring that no fluids can escape.

Figure 6:
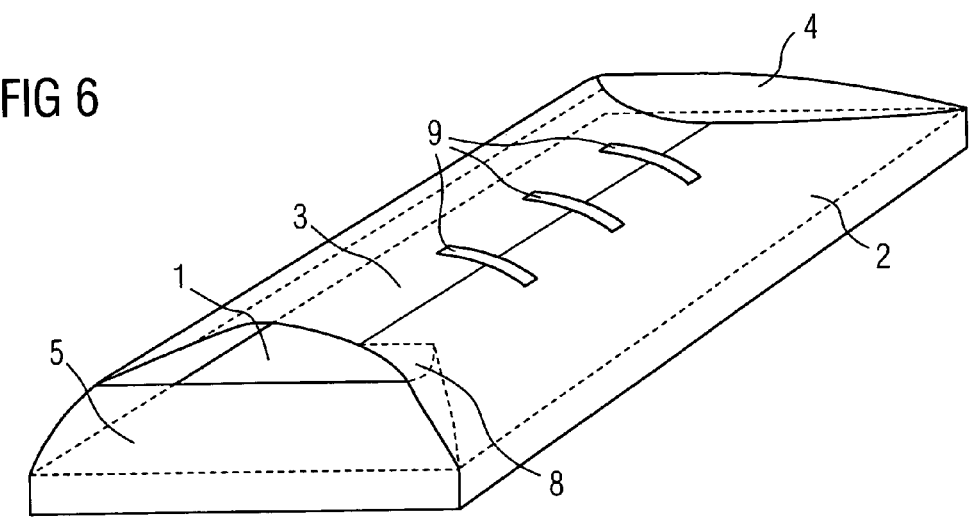

FIG. 6 shows the support mat 1 according to FIG. 5 in the folded over state, whereby the head section 5 and foot section 4 are inverted. It is evident here that the head section 5 does not have a separate hood in this embodiment, but is designed such that it forms the hood in conjunction with the lateral overhangs 2 and 3 and leaves an opening for the patient 16. In this view only one of the hidden gussets 8 is displayed for improved clarity.

The support mat 1 according to the invention fulfills all the desired requirements, in that it is made from relatively hard foam and is provided with a seamlessly welded polyurethane cover 22, which is provided around its lower side with skirt-like overhangs 2 to 5 of differing lengths, which are connected at the corners by means of gussets 8.

The overhangs 2 to 5 are designed such that the entire body length of the trauma patient 16 can be covered in an overlapping manner, the feet being covered in a correspondingly short manner and the head lying in a type of open hood 7.

During diagnosis and therapy on different modalities, the overhangs 2 to 5 are folded away from the trauma patient 16 so that they cover the modality 10 to 14 and possible escaping fluids do not penetrate the modality 10 to 14. In the folded over state, the mat protects the patient visually on the one hand and against heat loss on the other hand.

Furthermore the extremities are thus secured during transportation and also during a CT examination. During transportation the environment is protected from fluids, since the folded overhangs 2 to 5 form a type of sleeping bag by means of the gusset corners, so that no fluids escape. The open hood 7 facilitates unobstructed access to the head of the trauma patient 16 for anesthesiology processes.

One advantage of the support mat 1 according to the invention is that the modalities and environment are protected from escaping fluids during the diagnosis and therapy of trauma patients 16. Furthermore the trauma patient 16 can be supported without the risk of bedsores over long periods without impairing radiological imaging. The patient 16 is also protected against heat loss during support and during transportation by insulation provided by the support mat 1 and the fact that said patient is enveloped by the overhangs 2 to 5. The overhangs 2 to 5 similarly enable visual protection of the patient 16 during transportation and securing of the extremities during diagnosis methods (e.g. CT) and transportation.

The invention claimed is:

1. A support mat for a patient, comprising:
   a mat for accommodating the patient;
   a mat cover completely enclosing the mat in an interior volume completely defined by the mat cover, wherein the mat cover is formed by a welded mat cover sheet and is free of weld seams on its outer surface; and
   at least two mat cover side parts arranged at opposite ends of the mat, the mat cover side parts being connected to the mat cover and formed as overhangs.

2. The support that according to claim 1, wherein the mat cover side parts are integral parts of the mat cover.

3. The support mat according to claim 1, wherein the mat cover side parts, comprising a head section, a foot section, and the two mat cover side parts arranged at the opposite ends, are adapted to be connected to each other's ends to form an interior accommodation volume limited by a mat surface and a mat cover side parts surface continuously formed by the respective surfaces of the mat cover side parts.

4. The support mat according to claim 3, wherein the mat cover side parts are connected to each other using straps.

5. The support mat according to claim 1, wherein the mat cover is made from polyurethane.

6. The support mat according to claim 1, wherein the mat cover side parts are made from polyurethane.

7. The support mat according to claim 1, wherein the mat cover side parts have differing lengths.

8. The support mat according to claim 1, wherein the mat cover side parts are adapted to cover the entire length of the body of the patient lying on the support mat when the mat cover side parts are overlapped.

9. The support mat according to claim 1, wherein the mat cover side parts are connected to each other laterally using gussets.

10. The support mat according to claim 1, wherein the mat cover side parts comprise gussets arranged at corners of the side parts.

11. The support mat according to claim 1, wherein the mat is made from foam.

12. The support mat according to claim 1, wherein a head section of the support mat for accommodating the head of the patient is formed as an open hood.

13. The support mat according to claim 1, wherein the mat cover further includes a head section part formed as an overhang for covering the head of the patient.

14. The support mat according to claim 13, wherein the head section part includes an open hood attached to the head section part.

15. The support mat according to claim 13, wherein the mat cover further includes a foot section part formed as an overhang for covering the feet of the patient.

16. The support mat according to claim 15, wherein the foot section part has a shorter length than the mat cover side parts and head section part.

17. The support mat according to claim 15, wherein the mat cover side parts arranged at opposite ends, the head section part and the foot section part are folded away from the patient during diagnosis or therapy, the diagnosis or therapy conducted by utilizing an examination modality, the examination modality covered by the mat cover side parts or the head section part or the foot section part during diagnosis of therapy, wherein said mat cover side parts arranged at opposite ends, head section and foot section parts form a continuous mat cover side parts overhang effective to prevent the examination modality against fluids from the patient lying on the mat when said parts cover said examination modality, and effective to prevent escape of such fluids when folded over the patient.

18. The support mat according to claim 1, wherein the mat cover further includes a foot section part formed as an overhang for covering the feet of the patient.

19. The support mat according to claim 1, wherein the mat cover side parts are folded away from the patient during diagnosis or therapy, the diagnosis or therapy conducted by utilizing an examination modality, the examination modality covered by the mat cover side parts during diagnosis or therapy.

* * * * *